United States Patent [19]

Davies et al.

[11] Patent Number: 5,371,364

[45] Date of Patent: Dec. 6, 1994

[54] PRACTICAL IMPLEMENTATIONS FOR ION MOBILITY SENSOR

[75] Inventors: David K. Davies, Churchill Borough; John M. Zomp, North Huntingdon, both of Pa.

[73] Assignee: Thermo King Corporation, Minneapolis, Minn.

[21] Appl. No.: 19,051

[22] Filed: Feb. 18, 1993

[51] Int. Cl.$^5$ ............... B01D 59/44; H01J 49/00
[52] U.S. Cl. ............................... 250/287; 250/286; 250/423 P
[58] Field of Search ............ 250/286, 287, 423 P

[56] References Cited

U.S. PATENT DOCUMENTS

| | | | |
|---|---|---|---|
| 2,780,728 | 2/1957 | Langmuir | 250/286 |
| 2,950,387 | 8/1960 | Brubaker | 250/423 P |
| 3,593,018 | 7/1971 | Cohen . | |
| 3,621,239 | 11/1971 | Cohen . | |
| 3,624,389 | 11/1971 | Cohen et al. . | |
| 3,626,178 | 12/1971 | Cohen . | |
| 3,626,181 | 12/1971 | Wernlund . | |
| 3,626,182 | 12/1971 | Cohen . | |
| 3,629,574 | 12/1971 | Carroll . | |
| 3,639,757 | 2/1972 | Caroll et al. . | |
| 3,699,333 | 10/1972 | Cohen et al. . | |
| 3,812,355 | 5/1974 | Wernlund et al. . | |
| 4,259,573 | 3/1981 | Prober et al. . | |
| 4,390,784 | 6/1983 | Browning et al. | 250/286 |
| 4,445,038 | 4/1984 | Spangler et al. . | |
| 4,551,624 | 11/1985 | Spangler et al. . | |
| 4,733,086 | 3/1988 | Simmonds | 250/423 P |
| 4,777,363 | 10/1988 | Eiceman et al. . | |
| 5,184,015 | 2/1993 | Allman et al. | 250/287 |

Primary Examiner—Bruce C. Anderson

[57] ABSTRACT

A system for signalling the presence of selected ion species in a gaseous sample of an ion mobility sensor, having a unidirectional field provided between first and second electrodes positioned a selected distance apart. An ionization source generates ions in the sensor and a trigger controller allows ions to enter the region between the first and second electrodes at a time $t_1$. The ions then arrive at the second electrode at a time $t_2$. A transimpedance amplifier converts the ion charges to voltage signals. The presence of selected ion species is determined by circuitry that is activated by the trigger controller at $t_2$. The species are preferably analyzed by directing the amplifier output to an analog to digital converter and then to a digital signal processor. The ions may alternatively be analyzed by generating a logic pulse representing a selected ion species when the amplifier output exceeds a preset value. An alarm signal is output when the logic pulse is coincident at an AND gate with a logic pulse representing the species' travel time from the first electrode to the second electrode.

19 Claims, 5 Drawing Sheets

PRACTICAL IMPLEMENTATIONS FOR ION MOBILITY SENSOR

BACKGROUND OF THE INVENTION

1. Field of the Invention

This invention relates generally to devices for quantitatively measuring the concentrations of constituents of multicomponent gaseous samples, and more particularly to devices that conduct such measurements based upon the mobility of ions in a drift region.

2. Description of the Prior Art

Ion mobility spectroscopy is a powerful and well known method for providing quantitative measurements of the composition of a gaseous environment. In this context, the ion mobility sensor is usually designed for operation at atmospheric pressure although in principle it can operate at higher or lower pressures. The ion mobility sensor typically is comprised of two identifiable regions: (i) an ionization region where ions are formed representative of the gas sample to be analyzed, and (ii) a drift region into which the ions are injected and allowed to drift in an electric field before collection.

During the ions' drift in the drift region, the ions make many collisions with the sample gas and their motion in the electric field is characterized by the ion mobility. Since the ion mobility is a function of ion mass, ions of different mass segregate during their drift. Thus, by measuring the ion arrival time spectrum an the collector, a signature of the gas sample composition is obtained. Although positive ion spectra provide a selective signature for all gaseous species, the additional monitoring of negative ion spectra (for electronegative species) can provide supplementary information for either diagnostic or calibration purposes.

In currently available commercial instruments, the dimensions of the ionization region are comparable in magnitude to those of the drift region. The ions are produced primarily through ion-molecule reactions, where the impurity molecules of interest are ionized as a result of collisions with primary ions not necessarily derived from the background sample gas but rather from carrier gases deliberately introduced into the reaction region. These primary ions are produced as a result of collisions of beta particles emitted from a Ni-63 radioactive source (located within the ionization region) interacting with the sample and/or carrier gas. Since the beta particles are produced continuously, the ion production process is continuous and the species present in the ionization region represent an equilibrium composition developed over a relatively long time and which includes (deliberately in the case of the use of a carrier gas) ions produced as a result of ion molecule chemistry. Thus, in order to analyze the ions present in this equilibrium ion "sea", provision must be made to extract a pulse of ions into the drift region. This is usually accomplished using an electronic shutter whereby ions are only allowed into the drift region during the application of suitable electric potentials to the shutter electrodes. The detection limit of commercially available sensors depends on the particular species, and levels below one part per billion have been detected for certain organic molecules in air samples at atmospheric pressure without any preconcentration.

Although the ion mobility spectrometer is a well proven instrument, presently available models are relatively large, expensive and require ancillary gas supplies for calibration and for enhancing the ionization efficiency. In addition, present ion mobility spectrometers utilize a continuous nonadjustable ionization energy source. The ionization energy source is typically radioactive which is frequently undesirable. Because a continuous source has been presently used, a shutter is needed to inject a pulse of the total ions into the drift region. The shutter is typically a grid electrode that has a shutter voltage applied to in that injects the ions into the drift region.

The continuous source of the ionization energy is fixed and cannot be changed. Thus, when a complex molecule is being ionized, more than one species of ion may be generated if it interacts with sufficiently energetic electrons. This will disassociate the molecule into smaller fragments and some of those smaller fragments will also be ionized and so on. Therefore, there is very little control over which species of ion can be generated in current ionization methods.

It would also be advantageous to provide ion mobility sensors with a means for triggering an alarm when the concentration of a monitored species rises above some preset value. Alternatively, it would be advantageous to provide a means for the measuring of one or more different species.

SUMMARY OF THE INVENTION

I provide an ion mobility sensor having an ionization region and an ion drift region. The ionization region is preferably bounded by a grid cathode and an anode. It is into this ionization region that the gaseous sample enters, either by an opening to ambient in an open system or by a feed pipe in a closed system. In the context of positive ion sampling, the ion drift region is bounded by the grid cathode and a by a guarded ion collector. The ion collector consists of an electrode and its associated shield. Application of suitable potentials to this electrode arrangement establishes nominally uniform electric fields $E_i$ and $E_d$ in the ionization and drift regions respectively.

DC voltages applied to the anode, cathode and collector electrodes establish a unidirectional DC field across the entire sensor. A superimposed voltage pulse is provided at the anode which results in a field $E_i$ in the ionization region which is higher than the DC breakdown field but of sufficiently low amplitude and duration to avoid the development of an arc in the ionization region.

During the application of the voltage pulse, a pulse of ultraviolet (UV) radiation from a flash tube or other UV source irradiates the cathode grid, liberating a pulse of photo electrons from the cathode grid. Preferably, the anode is of a type that is semi-transparent to UV light, such as a grid anode or a semi-transparent conducting film anode. When the anode is semi-transparent, the UV light may be irradiated through the anode towards the cathode. The UV pulse liberates a pulse of photoelectrons from the cathode which in the presence of the pulsed high electric field generates a pulsed non-equilibrium discharge between the cathode and anode. The pulsed non-equilibrium discharge results from avalanching of the initial photoelectrons in ionizing collisions with the sample gas during the drift of the electrons to the anode, and gives rise to a pulse of ions characteristic of the sample gas in the volume between cathode and anode. The non-equilibrium discharge is characterized as that in which the mean energy of the electrons is considerably larger than that of the ions or neutral molecules. The avalanche growth of current is due to primary ionizing collisions between electrons and the sample gas during their drift to the anode as well as by secondary ionizing collisions between excited or ionized air molecules and the minority species. The minority species, in the case of large organic molecules, have relatively low ionization thresholds.

The positive ion pulse formed drifts toward the cathode grid and a fraction of the ions pass through the grid into the drift field region. After drifting across the drift region, these positive ions are collected by the ion collector. Because this collector is shielded from the drift region by a screened guard that is held at a potential consistent with the local electric field, the ions are only detected at the collector after they pass through the guard, and displacement current due to the motion of all ion species between the cathode and the shield is not observed by the detection circuit.

In general, the drift time of the different ion species is dependent on the charge and mass of the particular ions produced in the ionization region so that the detected ion signal comprises a series of pulses, each corresponding to a different species. Thus, provided that the mobilities of the different ions are known, the detector signal provides a signature of the different species present in the gaseous sample.

Although the electrodes of the preferred ion mobility sensor are configured to collect positive ions, it is understood that the polarity of the electrodes could be reversed for the collection of negative ions.

Once the ion pulses are received at the collector electrode as an electrical charge, the ion pulses are processed to evaluate the characteristics of the sample. The circuitry that processes the ion pulses is controlled by a trigger control. The trigger control also controls the timing of the UV pulse source and the pulsed voltage source such that the processing of electrical data representing the ion pulses will coincide with the receiving of that data from the collector electrode.

The first preferred implementation of the ion mobility sensor senses one or-more optionally variable, predetermined species in a specific gaseous sample. In the first implementation, an alarm is triggered if the concentration of the monitored species in the sample rises above some preset value. This value may be variable and may be different for the different species monitored.

The second preferred implementation of the ion mobility sensor involves integration of the sensor into a quantitative microprocessor-based system for the comprehensive measurement of one or more different selectable species. In either implementation, the trigger control is employed for controlling the timing of ion pulse creation in the sensor. The trigger control also controls the operation of the circuitry for evaluating the received ion pulses.

The sensor may be applied to detect a wide range of substances in many different environments, such as the presence of chemical and/or biological agents including impurities in refrigerant systems for the protection of compressors and other components, and refrigerated environments for optimizing cargo protection. The sensor may also be used to detect the presence of illegal drugs and explosives in containers and on personnel. Toxic storage, workplace or waste areas may be monitored as may areas for the presence of vapor fuels or other explosives. Anesthesia procedures may also be monitored.

Other details, objects and advantages of the invention will become apparent as the following description of certain present preferred embodiments thereof proceeds.

DETAILED DESCRIPTION OF THE PREFERRED EMBODIMENT

Figure 1:
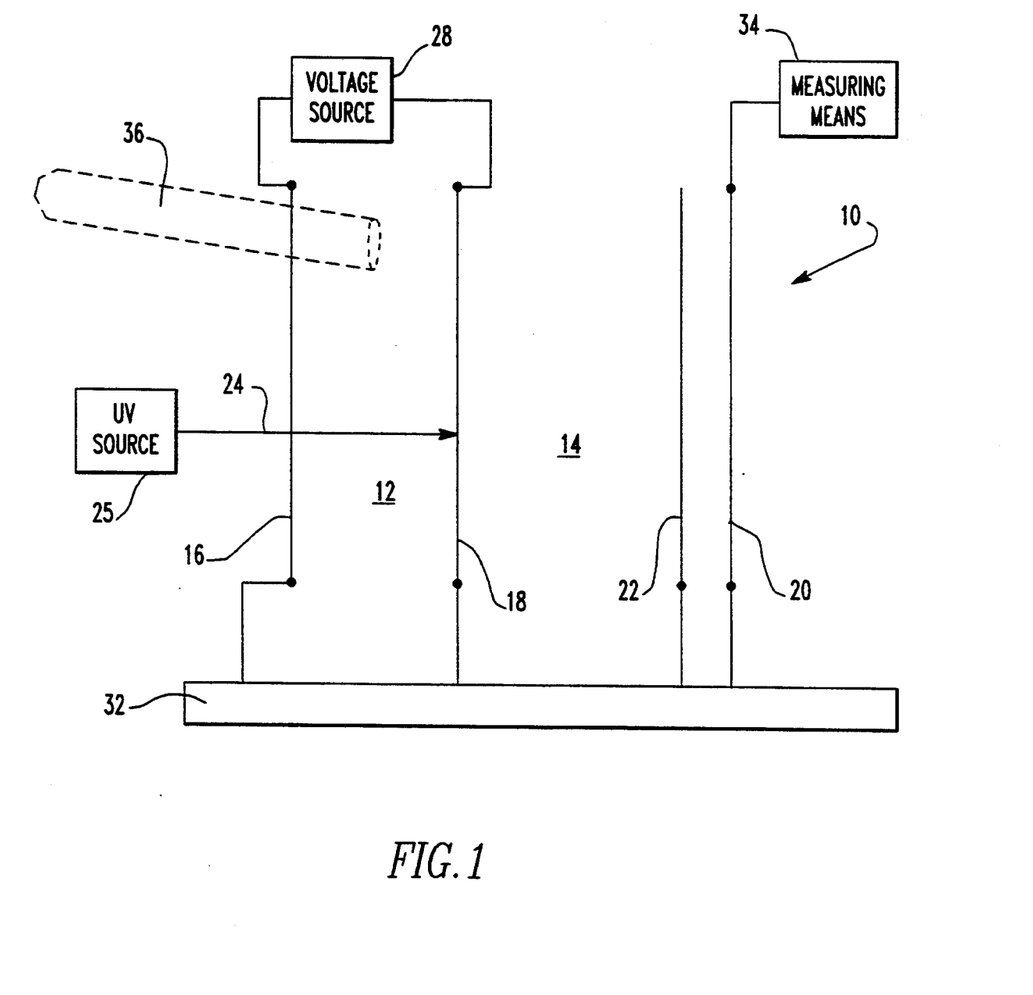
FIG. 1 is a diagrammatic representation of the electrode arrangement of the preferred ion mobility sensor for positive ion sampling.

Referring first to FIG. 1, an ion mobility sensor 10 has two connected regions: an ionization region 12 and a drift region 14. FIG. 1 shows a preferred electrode arrangement which defines the two regions 12, 14 of the sensor 10. The ionization region 12 is bounded by an electrode 16 and a meshed electrode 18. The manner in which the gaseous sample enters the ionization region 12 depends upon whether the sensor 10 is embodied as an open system or as a closed system. If the sensor 10 is embodied as an open system, the area between the grid electrode 18 and the electrode 16 is unconfined and the ambient gas may freely enter the ionization region 12. If the sensor 10 is embodied as a closed system, the sensor 10 would have walls confining the area between the electrode 18 and the electrode 16. Thus, in a closed system, ambient gas is not free to enter the ionization region 12. Any gaseous sample that is to be analyzed must be entered into the ionization region by a feed pipe 36 (shown in dotted line in FIG. 1).

The gaseous sample is entered into the ionization region 12 between the electrode 16 and the electrode 18. The electrode grid 18 separates the ionization region 12 from the drift region 14, and thus also bounds one end of the drift region 14. A shielded collector electrode 20 bounds the end of the drift region 14 opposite no the electrode 18. Although it need not be, the drift region 14 is preferably bounded by walls so as to prevent the entrance or exit of ions from the drift region 14. A meshed shield electrode 22 is preferably located adjacent to the collector electrode 20 and lies between the collector electrode 20 and the electrode 18.

Figure 2:
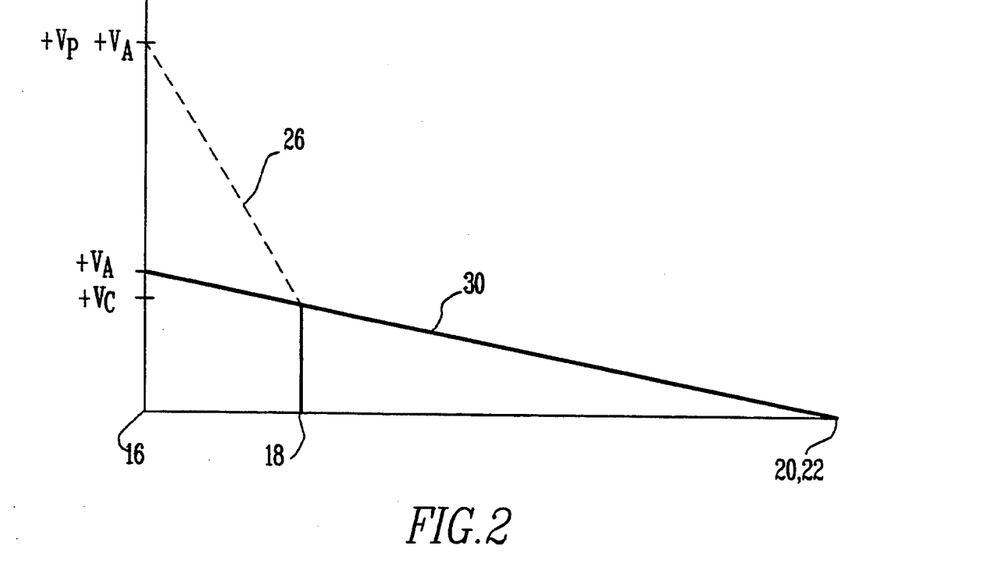
FIG. 2 is a diagrammatic representation of the potential distribution of the preferred ion mobility sensor.

Application of suitable potentials to this electrode arrangement establishes electric fields across the sensor 10. For positive ion sampling, DC voltage potentials 30, as depicted in FIG. 2, are applied by a potential source 32 at the anode 16, the cathode 18 and the shielded collector electrodes 20, 22. Thus, the anode 16 has a voltage of $V_a$, the cathode 18 has a voltage of $V_c$ and the ion collector components (the collector electrode 20 and the shield 22) have a voltage of $V_{ic}$ due to the potential source 30. The applied voltage potentials 30 result in a unidirectional DC drift field $E_d$ across the sensor 10. The drift field $E_d$ is capable of carrying ions from the ionization region 12 through the drift region 14 to the collector electrode 20. In general, the drift time of the different ion species is dependent upon the charge and mass of the particular ions produced in the ionization region. The magnitude of the field $E_d$ is low enough so as not to produce ions in the drift region as a result of electron molecule collisions.

A voltage pulse 26 (depicted as a dotted line in FIG. 2) from an impulse generator 28 is superimposed upon the drift voltage 30 at the anode 16. The superimposed high voltage pulse 26 results in a total anode voltage designated as of $V_a+V_p$ in FIG. 2. The increased voltage applied at the anode 16 results in a field $E_i$ in the ionization region 12 between the anode 16 and the cathode 18. The magnitude of the voltage pulse 26 is selectable, but is chosen so that the generated field $E_i$ is higher in magnitude than the ionizing DC breakdown field of the sample but is also of sufficiently low amplitude and duration so as to avoid the development of an arc in this region. The application of the pulsed voltage 26 results in the potential of the anode 16 being equal to the DC potential 30 at the anode 16 plus the voltage pulse 26.

During the application of the voltage pulse 26, a pulse 24 of ultraviolet (UV) radiation from a suitable UV source 25, such as a flashtube, irradiates the cathode grid 18. The intensity of the UV pulse is selectable and defines the number of photoelectrons released from the cathode of the ionization region 12. Preferably, the anode 16 is of a type that is semi-transparent to UV light, such as a semi-transparent conducting film anode or preferably a grid anode. When the anode 16 is semi-transparent, the UV light pulse 24 may be irradiated through the anode 16 towards the cathode grid 18. By irradiating through the anode 16, the UV source 25 may be located outside of the ionization region 12 while still directing the UV pulse 24 upon the face of the cathode 18.

When the UV pulse 24 reaches the cathode grid 18, the UV light 24 liberates a pulse of photoelectrons from the cathode 18. The greater the intensity of the UV pulse, the larger the number of electrons liberated. The electrons then drift toward the anode 16 creating an avalanche of electron generation. The voltage pulse 26 raises the mean energy of the electrons liberated from the cathode 18 above the ionization level and creates a nonequilibrium discharge situation. With a nonequilibrium discharge, the electrons are at much higher energy than are the heavier particles, i.e., the ions and the neutral particles, resulting in ionization.

Since the disclosed ion mobility sensor 10 provides a pulsed source of ions, a shutter is not needed. While the electrons travel towards the anode 16, the positive ions move towards the cathode grid 18. Because the cathode 18 is a grid, there are gaps between the solid portions of the grid. Those ions which arrive at a solid part of the cathode 18 will get collected. Those ions that arrive at a gap in the cathode grid 18 will be carried through the gap due to the drift field $E_d$. At the time in which the positive ions arrive at the cathode 18, the voltage pulse 26 is off and the steady DC drift field $E_d$ carries the ions.

Because the anode 16, cathode 18, and shield 22 are preferably grids, the UV pulse 24 irradiates the anode 16, cathode 18, shield 22 and collector electrode 20. Any photoelectrons emitted from the anode 16 are prevented from leaving the anode by the applied field $E_i$. However, photoelectrons emitted from the shield 22 and collector electrode 20 begin to drift in the applied drift field $E_d$ towards the cathode 18. In applications in which there are no electronegative species present, these electrons (because of their large drift velocity) arrive at the cathode 18 during the voltage pulse 26 and thereby augment the photoemission from the cathode 18. In applications (such as air) in which there is a large electronegative constituent, electrons emitted from the shield 22 and the collector electrode 20 become attached to form negative ions after drifting a very small fraction of the drift region because of the large three-body attachment coefficient in oxygen at the low applied drift field $E_d$. In this case, any negative charge reaching the ionization region 12 that originates from the shield 22 and collector electrode 20, does so a substantial time after the duration of the voltage pulse 26. In any event, the negative charge arrives in the form of negative ions and therefore, cannot give rise to spurious ionization pulses.

An increase in the ionization field $E_i$ increases the mean energy of the electrons and, therefore, increases the amount of ionization. However, such a variation in the electron distribution also varies the ratio of the coefficients of the different ionization species derived either from different parent molecules in a mixture or from the same molecule as a result of different fragment ions. This ability to tailor the ionization probability among the different neutral gas constituents is an important feature of the disclosed ion mobility sensor 10. Thus, by deliberately varying the field $E_i$ in the ionization region 12, the probability of ionization of ions having different ionization thresholds can be varied. By providing relatively low energy with the voltage pulse 26, those ions that require the least amount of energy to ionize will ionize. By increasing the value of the voltage pulse 26, and therefore increasing the magnitude of the ionization field $E_i$, higher ionization levels of a given molecule will be reached, accessing different ions. This provides a secondary means of ion discrimination in operation of the sensor 10 allowing the ionization of selected ion species from a sample.

In the nonequilibrium discharge situation, the electrons are of much higher energy than are the heavier particles of either the ions that are generated or the background gas. The ions are at thermal energy and their energy is determined by the background temperature. The mean energy of the electrons in the ionization region 12 is determined solely by the ratio of the electric field $E_i$ between the anode 16 and the cathode 18 divided by the total gas density of the ionization region 12. Therefore, the mean energy of the electrons may be adjusted by adjusting the magnitude of the voltage pulse 26 applied to the anode 16. Also, the number of electrons liberated from the cathode 18 is dependent upon the amount of UV light emitted in each pulse 24. The amount of ionization that occurs to the gaseous sample is dependent upon the magnitude of the electric field $E_i$ produced by the voltage pulse 26. Thus, by offering independent control of both the magnitude of the UV pulse and the magnitude of the voltage pulse, the amount and extent of ionization may be effectively controlled.

The shield 22 is preferably a meshed or grid plate that has a potential associated with it that will keep the drift field $E_d$ uniform. The collector electrode 20 operates at near ground potential preserving the uniformity of the drift field $E_d$. The shield 22 protects the collector electrode 20 from detecting the motion of any induced charge which would otherwise appear on the collector electrode 20. Otherwise, the collector electrode 20 would detect a constant current which would then decrease in steps, where each step would correspond to the collection of a particular species of ion.

Thus, the shield 22 effectively differentiates the current so that no signal is detected at the collector electrode 20 charge passes through the shield 22. Thus, the collector electrode 20 detects a series of electrical pulses in which each pulse is the current due to a given species of ion. Therefore, provided that the mobilities of the different species are known, the pulses collected at the collector electrode 20 provide a signature of the different species present in the sample gas.

Connected to the collector electrode 20 is a means 34 for detecting and measuring the current generated by the ions reaching the collector electrode. Such means involve connecting a transimpedance amplifier to the collector electrode. The transimpedance amplifier converts the incoming ion charge to a voltage signal.

Although the electrodes of the preferred ion mobility sensor are configured to collect positive ions, it is understood the polarity of the electrodes could be reversed for the collection of negative ions.

Figure 3:
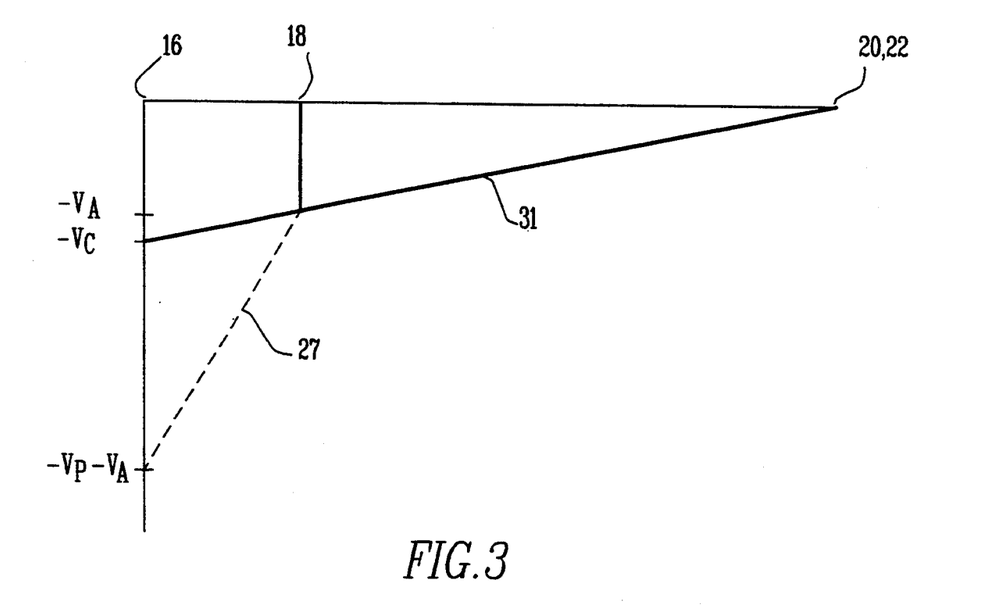
FIG. 3 is a diagrammatic representation of the potential distribution of the preferred ion mobility sensor for negative ion sampling.

For negative ion collection, the potential distribution is as shown in FIG. 3 where now electrode 16 becomes the cathode and electrode 18 becomes the anode of the ionization region 12. Application of negative polarity potentials 31, as depicted in FIG. 3, from source 32 result in a voltage of $-V_a$ at the anode 18, and $-V_c$ at the cathode 16, and ensure a unidirectional DC electric field across the sensor. A negative polarity voltage pulse 27 (depicted as a dotted line in FIG. 3) from generator 28 is superimposed on the voltage of electrode 16 and results in a total cathode voltage designated at $-V_a-V_p$ in FIG. 3. The photoelectron pulse released from the cathode 16 as a result of irradiation by the UV pulse during the application of the voltage pulse 27 triggers a non-equilibrium discharge between electrodes 16 and 18 which define the ionization region. Negative ions formed in the ionization region then drift towards electrode 18 and a fraction of them continue to drift through the meshed anode 18 under the influence of the DC drift field and enter the drift region. Once in the drift region the negative ions continue to drift toward the collector and are eventually sampled in a similar way to that described earlier for positive ions. The establishment of a non-equilibrium discharge in the ionization region ensures the production of negative ions formed by the dissociative attachment process as well as by electron capture by the parent molecule.

Figure 4:
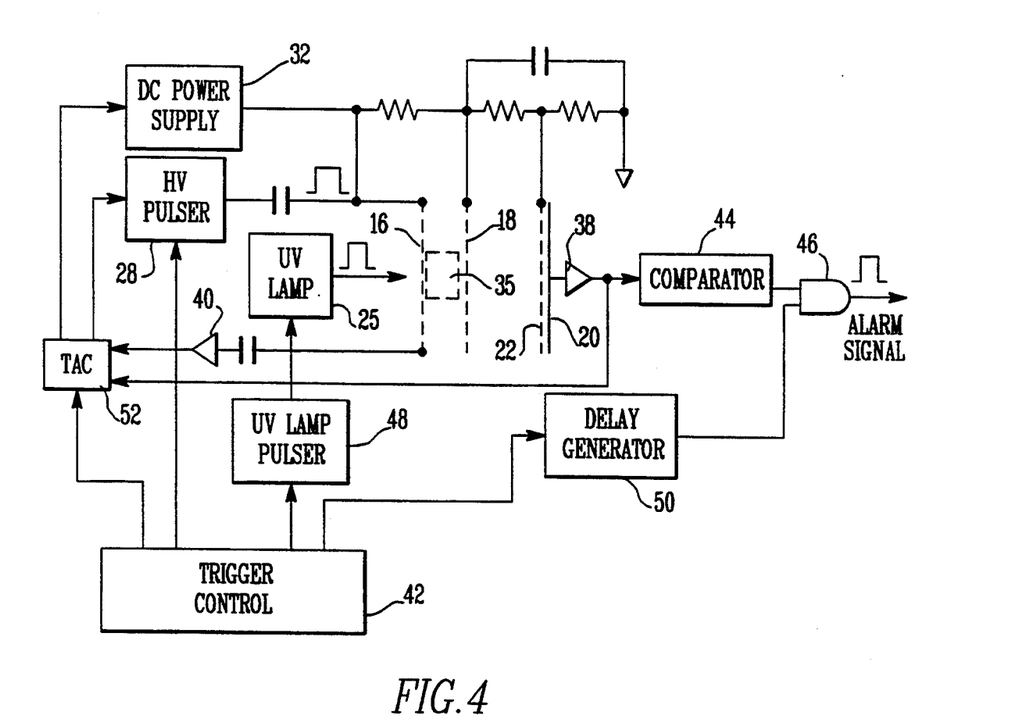
FIG. 4 is a diagrammatic representation of the alarm circuitry for the first preferred implementation of the ion mobility sensor.

Referring next to FIG. 4, a diagrammatic representation of an ion mobility sensor is shown in which a first preferred implementation, an alarm system, is employed. The electrodes are configured for the case where a single positive ion species is monitored in an electronegative sample, although as already noted, the polarity of the electrodes could be reversed for monitoring negative ion species. A positive DC voltage is applied to the electrodes 16, 18, 20 and 22 with the appropriate potentials for providing a unidirectional, approximately uniform electrical field from the anode 16 to the collector electrode 20. The value of the electric field in the drift area $E_d$ is such as to ensure than between the anode 16 and the collector electrode 20 the ions are in thermal equilibrium with the sample gas. A capacitor connected across the drift region is use to maintain a constant field $E_d$ in the region.

A voltage pulse 26 is capacitively coupled to the anode 16 from a high voltage pulser 28 such as a pulse transformer, triggered from the trigger controller 42. The amplitude of the voltage pulse 26 is sufficiently high so that the ratio of the total electrical field between the anode 16 and the cathode 18 to the total sample gas density N is above the ionization threshold value for the particular sample under investigation. Both the DC and pulse amplitudes are variable.

Figure 5:
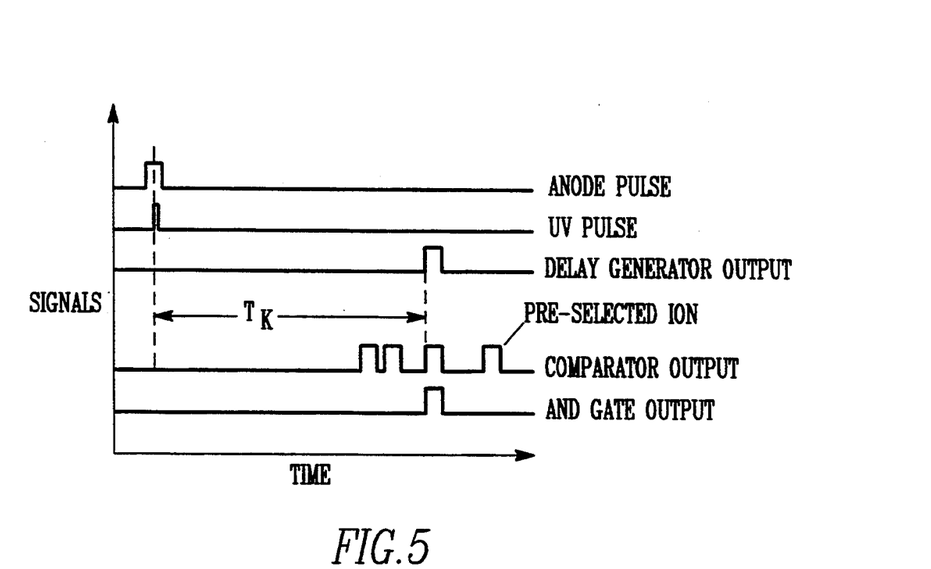
FIG. 5 is a diagrammatic representation of the alarm signal timing for the first preferred implementation of the ion mobility sensor.

A UV lamp pulser 48 is triggered by a pulse from the trigger controller 42 and provides the drive power for the UV light source 25 which may, for example, be a xenon flashtube equipped with a UV transmitting window. The resulting UV pulse is arranged to be delayed with respect to the anode voltage pulse and contained within the anode pulse envelope duration as indicated in the timing diagram of FIG. 5. The incidence of the resulting UV pulse at the cathode 18 gives rise to a pulsed discharge which is self-quenched on decay of the voltage pulse 26. The relative position of the UV pulse 24 with respect to the voltage pulse 26, together with the amplitude and width of the voltage pulse 26 are adjusted for optimum ion discharge intensity for a predetermined sensitivity within the limitation that the discharge not develop into an arc.

The electrodes are coupled to a first and a second transimpedance amplifiers 38, 40. The first transimpedance amplifier 38 is coupled to the collector electrode 20 for positive ion species measurement.

The output from the first transimpedance amplifier 38 is fed to a comparator set 44 to provide a standard logic pulse when the detected signal is above a preset level. Thus, the output from the comparator 44 consists of a sequence of logic pulses corresponding to the arrival of pulses of different positive ion species at the collector electrode 20 when the amplitudes of these pulses are above the preset level. The output from the comparator 44 is then connected to one input of an AND gate 46. The other input of the AND gate 46 is connected to a delay generator 50 which outputs a logic pulse at a predetermined time following the UV pulse trigger 48. This predetermined time corresponds to the known transit time of the monitored ion species. Thus, if both pulses are coincident at the AND gate 46 an output is derived from the AND gate 46 which may be used to trigger an appropriate alarm 54.

Figure 6:
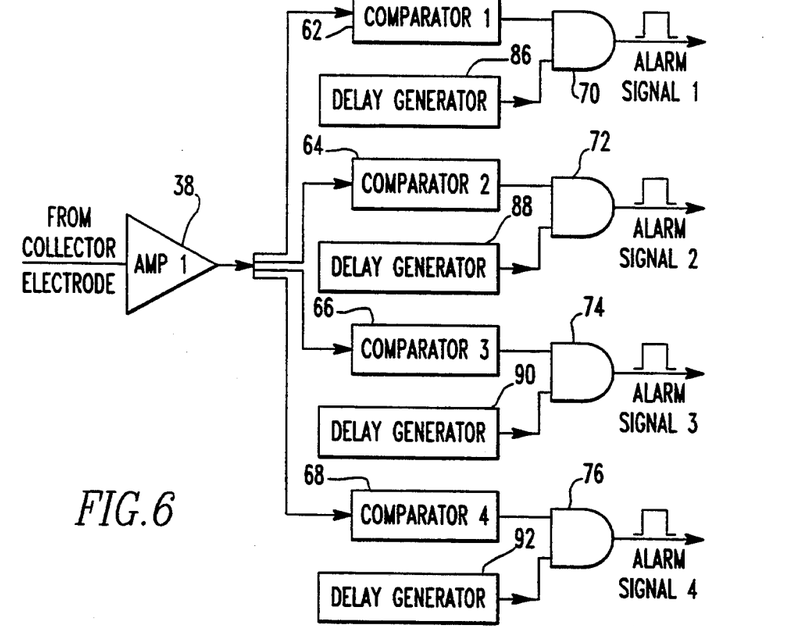
FIG. 6 is a diagrammatic representation of the alarm circuitry for an alternative to the first preferred implementation of the ion mobility sensor.

A variation of the first preferred implementation of the ion mobility sensor is shown in FIG. 6. In this variation, the simultaneous monitoring of n multiple ion species is accomplished where the different species trigger alarms when the levels of these species rise above different preset levels. An example of this system for the case of n=4 is shown in FIG. 6. The output from the first transimpedance amplifier 38 is directed to four different comparators 62, 64, 66 and 68 in which the individual alarm limit levels are set. Each comparator 62, 64, 66, 68 feeds an input of a respective AND gate 70, 72, 74, 76. Delay generators 86, 88, 90, 92 feed the other input of the respective AND gates 70, 72, 74, 76. The delay generators 86, 88, 90, 92 may be part of one delay generator unit or may be separate units similar to the delay generator 50 of FIG. 4. Each AND gate is set to emit an alarm pulse at the coincident arrival of pulses from the comparators and appropriately delayed pulses from the delay generator corresponding to the specific transit times of the different ion species. One of the channels shown in FIG. 6 may alternatively be used to provide a test signal by detecting an ion characteristic of the majority sample and which should always be present regardless of minority impurities.

Figure 7:
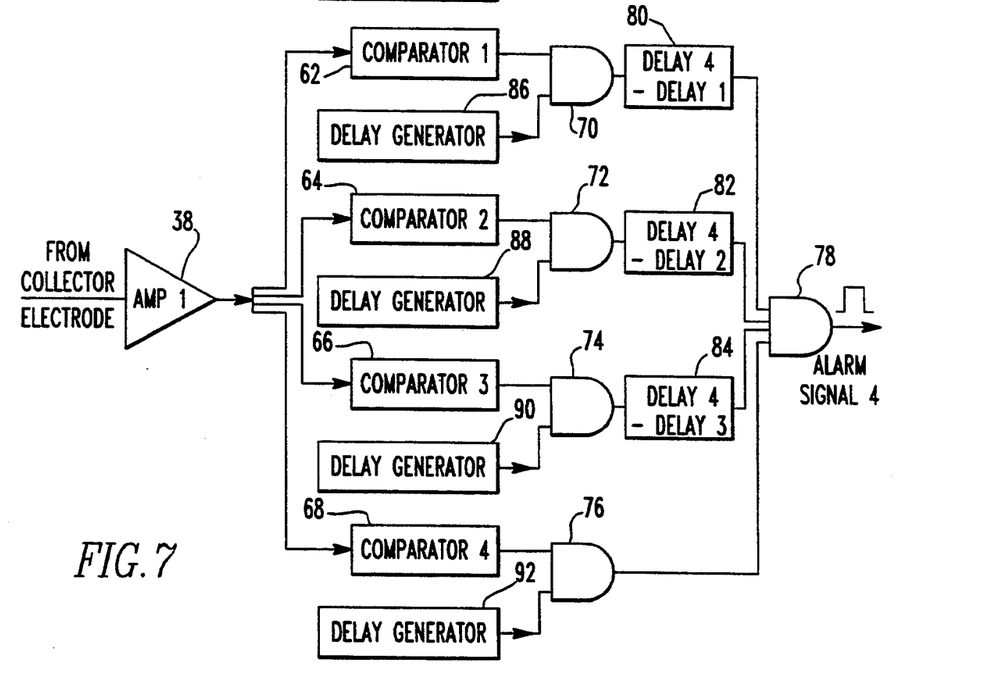
FIG. 7 is a diagrammatic representation of the alarm circuitry of another alternative to the first preferred implementation of the ion mobility sensor.

Another variation of the first implementation is the alarm system shown in FIG. 7. In this alternative, the alarm signal is output only if, for example, a number of different ion species (four species being demonstrated in FIG. 7) derived from the same or related impurity molecules are detected. In this arrangement, the outputs from the individual AND gates 70, 72, 74, 76 following the comparators 62, 64, 66, 68 and delay generators 86, 88, 90, 92, respectively, are fed after suitable delay to a multi-input AND gate 78. These delays 80, 82, 84 are added to all but a reference species and are such so as to compensate for the different known transit times of specific ion species so that all input signals to the multi-input AND gate 78 arrive simultaneously. This may be accomplished by adding a delay to the signals of the species equal to the delay of a reference species minus that species' delay. For example, if the species preset at comparator 68 is the reference and has a delay (transit time) of $t_4$, the species of comparator 62 which has a delay of $t_1$, has a delay added to it equal to $t_4-t_1$ (shown as 80 in FIG. 7). When this delay is added to $t_1$, the total delay for the species of comparator 62 is $t_1+(t_4-t_1)$ which is $t_4$. This step would also be performed on the species of comparators 64 and 66. Thus, for the case in which the species of comparator 68 is the reference, all species will be delayed by the same time, $t_4$. It is preferable for the species having the longest transmit time to be chosen as the reference. When all four input signals to the multi-input AND gate 78 arrive simultaneously, an output alarm pulse is triggered. This system would be incorporated to reduce the occurrence of false alarms due to possible interference from unrelated species.

In the alternative shown in FIG. 7, the control of the sensor may either be local, such as by toggling a switch, or remote. In the latter case, the control signal can be carried by conventional cable, fiber optic cable, RF telemetry or any convenient means depending on the particular nature of the sensor environment. It is distinctly understood that although four comparators for four different species have been discussed in the alternatives of FIGS. 6 and 7, the number of comparators utilized, and the number of species monitored is not limited to four but may be any number.

Figure 8:
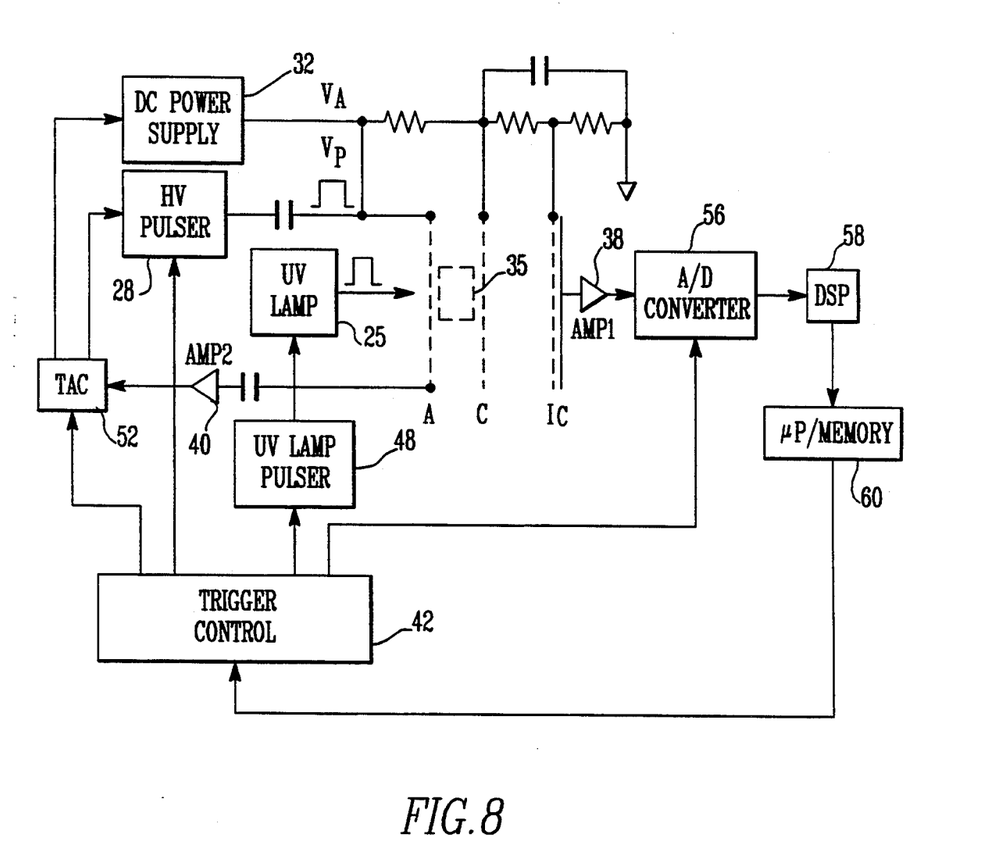
FIG. 8 is a diagrammatic representation of the circuitry for a second preferred implementation of the ion mobility sensor.

A second preferred implementation is shown in FIG. 8. This embodiment integrates the sensor into a quantitative microprocessor-based system for the comprehensive measurement of one or more different programmable species. The electronic arrangement for this embodiment is similar to that of the embodiment shown in FIG. 4 except that the comparator and AND gate have been replaced by an analog-to-digital converter (A/D converter) 56 and some kind of microprocessor 58.

In addition to triggering the ionization, the trigger control 42 triggers the A/D converter 56 to start accepting data. The A/D converter 56 then receives the output voltage from the first transimpedance amplifier 38 and digitizes it. The digitized signal is then processed in the digital signal processor 58. The signal processing could involve providing look up tables in memory 60 that represent various ion species. The digitized signals derived from the collected ions would then be compared to the look up table values. This comparison would allow determination of which species were present in a sample and in what amounts.

It is preferred that the voltage pulser and the UV pulse source may operate to repetitively pulse the voltage and UV light pulses. It is also preferred that the digital signal processor and memory unit cooperate to store the digital output from the analog to digital converter and provide signal averaging of the ion signals and thereby improve the signal/noise ratio.

It is understood that the above-described implementations are not limited to the preferred ion mobility sensor but may be utilized in any ion mobility sensor that has an ionization region and a collector electrode. Ion mobility sensors that do not employ pulsed ionization means instead often utilize a continuous ionizing source 35 (shown in dotted line often in FIGS. 4, and 8) such as Ni-63. Sensors using continuous ionization means typically use a shutter electrode which may be electrode 18 to inject the ions into the drift region in pulses. In this type of sensor, the trigger controller triggers the shutter electrode rather than the voltage and UV pulsers, however, the implementations would otherwise operate substantially identically as in the pulsed ionization case described above. Thus, regardless of the type of ionization means chosen or of the electrode polarization, species of ions may be quantitatively and qualitatively monitored.

While a present preferred embodiment of the invention has been shown, it is distinctly understood that the invention is not limited thereto but may be otherwise variously embodied within the scope of the following claims.

We claim:

1. A system for signalling the presence of selected ion species in a gaseous sample of an ion mobility sensor, a sensor having an ionization region being connected to a drift region, the sensor comprising:
   (a) a boundary grid electrode providing a boundary between the ionization region and the drift region;
   (b) a first electrode positioned at an end of the ionization region opposite to to the boundary electrode;
   (c) a second electrode at an end of the drift region opposite to the boundary electrode wherein a voltage potential is applied to the first electrode, second electrode and boundary electrode creating a unidirectional electric field between the electrodes;
   (d) an ionization source for generating ions in the sensor proximate the boundary electrode at a time $t_1$, wherein the ions travel through the drift region and arrive at the second electrode at a time $t_2$, wherein the ionization source comprises:
      (i) a UV light source for directing a pulse of UV light at one of the first electrode and the boundary electrode; and
      (ii) a voltage source for applying a voltage pulse to the first electrode coincident with the UV pulse;
   (e) a transimpedance amplifier connected to the second electrode for converting the ion charges to voltage signals; and
   (f) analyzer circuitry for determining the presence of selected ion species, the analyzer circuitry being activated at time $t_2$.

2. The system of claim 1 further comprising a trigger controller connected to at least one of the boundary electrode and the ionization source for causing ions to enter the drift region.

3. The system of claim 1 wherein the UV light source is a xenon flashtube.

4. The system of claim 1 wherein the voltage source is a pulse transformer.

5. The system of claim 1 wherein the analyzer comprises:
   (a) an analog to digital converter connected to the transimpedance amplifier, the analog to digital converter converting the voltage signals to digital units; and
   (b) a digital signal processor connected to the analog to digital converter for processing the digital units.

6. The system of claim 5 further comprising a memory unit connected to the signal processor for storing the processed digital units.

7. The system of claim 1 further comprising at least one comparator set which receive the voltage signals from the transimpedance amplifier, each at lease one comparator set generating a respective logic pulse representing a selected ion species when the voltage signals exceed a preset value.

8. The system of claim 7 wherein the analyzer circuitry comprises:
   (a) a delay generator connected to the trigger controller, the delay generator producing a selected number of logic pulses, each logic pulse representing a respective ion species, each logic pulse being produced at a time after the ionization source has been activated representing that ion species' travel time from the boundary electrode to the second electrode; and
   (b) at least one AND gate, each at least one AND gate having first and second inputs and an output, the first input of each at least one AND gate being connected to a respective comparator set so as to receive the logic pulses of a selected ion species, and the second input being connected to the delay generator so as to receive the delay generator logic pulse corresponding to the selected ion species, wherein whenever the delay generator logic pulse and the comparator set logic pulse coincide at any of the at least one AND gates, a signal is output from the AND gate output.

9. The system of claim 8 further comprising a multi-input AND gate wherein each input of the multi-input AND gate is fed from the output of the at least one AND gate after being delayed so as to provide coincident arrival of the signals at the inputs, such that when each input of the multi-input AND gate receives a signal, a signal is output from the multi-input AND gate output.

10. The system of claim 1 wherein the gaseous sample is provided from a refrigeration system so as to signal the presence of contaminants in the refrigeration system.

11. The system of claim 1 wherein the gaseous sample is provided from a cargo container ambient so as signal the presence of contaminants in the cargo container ambient.

12. The system of claim 1 wherein the gaseous sample is provided from a workplace environment so as to signal the presence of contaminants in the workplace environment.

13. An alarm system for an ion mobility sensor for detecting the presence of a selected species in a gaseous sample, the sensor having a drift region being connected to an ionization region, the system comprising:
   (a) a boundary grid electrode providing a boundary between the ionization region and the drift region;
   (b) a first electrode positioned at an end of the ionization region opposite to the boundary electrode;
   (c) a second electrode provided at an end of the drift region opposite to the boundary electrode wherein a voltage potential is applied to the electrodes creating a unidirectional electric field between the electrodes;
   (d) a UV light source for directing a pulse of UV light at one of the first electrode and the boundary electrode;
   (e) a voltage source for applying a voltage pulse to the first electrode coincident with the UV pulse;
   (f) a trigger controller for driving a UV light source at selected instances to produce the UV light pulses, the trigger controller also driving a voltage source at selected instances to produce voltage pulses, wherein the voltage and UV pulses generate ions proximate the boundary electrode, which ions travel through the drift region toward the second electrode;
   (g) a first transimpedance amplifier coupled to the second electrode, the first transimpedance amplifier converting charges of the ions received at the second electrode to voltage signals;
   (h) a comparator set connected to the first transimpedance amplifier, the comparator set generating a sequence of logic pulses when the voltage signal from the amplifier exceeds a preset value;
   (i) an AND gate having first and second inputs and having an output, the first input of the AND gate being connected to the comparator set so as to receive the logic pulses;
   (j) a delay generator connected to the trigger controller, the delay generator producing a logic pulse representing a selected ion species at a selected time after the UV light pulse, the delay generator further being connected to the second output of the AND gate, wherein whenever the delay generator logic pulse and the comparator set logic pulse coincide, an alarm signal is generated at the AND gate output; and
   (k) an alarm connected to the AND gate which alarm is activated by the alarm signal.

14. A system for determining the amount of selected species in a gaseous sample introduced into an ion mobility sensor, the sensor having a drift region being connected to an ionization region, the system comprising:
   (a) a boundary electrode providing a boundary between the ionization region and the drift region;
   (b) a first electrode provided at an end of the ionization region opposite to the boundary electrode;
   (c) a second electrode provided at an end of the drift region opposite to the boundary electrode wherein a voltage potential is applied to the electrodes creating a unidirectional electric field between the electrodes;
   (d) a UV light source for directing a pulse of UV light at one of the first electrode and the boundary electrode;
   (e) a voltage source for applying a voltage pulse at the first electrode coincident with the UV pulse;
   (f) a trigger controller for driving a UV light source at selected instances to produce the UV light pulses, the trigger controller also driving a voltage source at selected instances to produce voltage pulses, wherein the voltage and UV pulses generate ions proximate the boundary electrode which travel through the drift region toward the second electrode;

(g) a first transimpedance amplifier coupled to the second electrode, the first transimpedance amplifier converting the charges of the ions received at the second electrode to voltage signals;

(h) an analog to digital converter being connected to the first transimpedance amplifier and to the trigger control so as to convert the voltage signals received from the amplifier to analog signals when activated by the trigger control; and (i) a digital signal processor connected to the analog to digital converter for processing the digital signals received from the converter.

15. The system of claim 14 further comprising a memory unit connected to the signal processor for storing analog data.

16. The system of claim 14 further comprising means for repetitively pulsing the UV and voltage pulses.

17. The system of claim 16 further comprising means for storing the output from the analog to digital converter and to provide signal averaging of the ion signals so as to improve the signal to noise ratio.

18. An alarm system for an ion mobility sensor for detecting the presence of a selected species in a gaseous sample, the sensor having a drift region being connected to an ionization region, the system comprising:

(a) a boundary grid electrode providing a boundary between the ionization region and the drift region;

(b) a first electrode positioned at an end of the ionization region opposite to the boundary electrode;

(c) a second electrode provided at an end of the drift region opposite to the boundary electrode wherein a voltage potential is applied to the electrodes creating a unidirectional electric field between the electrodes;

(d) a UV light source for directing a pulse of UV light at one of the first electrode and the boundary electrode;

(e) a voltage source for applying a voltage pulse to the first electrode coincident with the UV pulse;

(f) a trigger controller for driving a UV light source at selected instances to produce the UV light pulses, the trigger controller also driving a voltage source at selected instances to produce voltage pulses, wherein the voltage and UV pulses generate ions proximate the second electrode, which ions travel through the drift region toward the first electrode;

(g) a second transimpedance amplifier coupled to the first electrode, the second transimpedance amplifier converting charges of the ions received at the first electrode to voltage signals;

(h) a comparator set connected to the second transimpedance amplifier, the comparator set generating a sequence of logic pulses when the voltage signal from the amplifier exceeds a preset value;

(i) an AND gate having first and second inputs and having an output, the first input of the AND gate being connected to the comparator set so as to receive the logic pulses;

(j) a delay generator connected to the trigger controller, the delay generator producing a logic pulse representing a selected ion species at a selected time after the UV light pulse, the delay generator further being connected to the second output of the AND gate, wherein whenever the delay generator logic pulse and the comparator set logic pulse coincide, an alarm signal is generated at the AND gate output; and (k) an alarm connected to the AND gate which alarm is activated by the alarm signal.

19. A system for determining the amount of selected species in a gaseous sample introduced into an ion mobility sensor, the sensor having a drift region being connected to an ionization region, the system comprising:

(a) boundary electrode providing a boundary between the ionization region and the drift region;

(b) a first electrode provided at an end of the ionization region opposite to the boundary electrode;

(c) a second electrode provided at an end of the drift region opposite to the boundary electrode wherein a voltage potential is applied to the electrodes creating a unidirectional electric field between the electrodes;

(d) a UV light source for directing a pulse of UV light at one of the first electrode and the boundary electrode;

(e) a voltage source for applying a voltage pulse at the first electrode coincident with the UV pulse;

(f) a trigger controller for driving a UV light source at selected instances to produce the UV light pulses, the trigger controller also driving a voltage source at selected instances to produce voltage pulses, wherein the voltage and UV pulses generate ions proximate the second electrode which travel through the drift region toward the first electrode;

(g) a second transimpedance amplifier coupled to the first electrode, the second transimpedance amplifier converting the charges of the ions received at the first electrode to voltage signals;

(h) an analog to digital converter being connected to the second transimpedance amplifier and to the trigger control so as to convert the voltage signals received from the amplifier to analog signals when activated by the trigger control; and (i) a digital signal processor connected to the analog to digital converter for processing the digital signals received from the converter.

* * * * *